(12) United States Patent
Lo

(10) Patent No.: US 11,998,173 B1
(45) Date of Patent: *Jun. 4, 2024

(54) IMAGING SYSTEM AND METHOD

(71) Applicant: Gustav Lo, Petoskey, MI (US)

(72) Inventor: Gustav Lo, Petoskey, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/210,830

(22) Filed: Jun. 16, 2023

Related U.S. Application Data

(63) Continuation of application No. 17/704,360, filed on Mar. 25, 2022, now Pat. No. 11,678,789, which is a continuation of application No. 16/893,927, filed on Jun. 5, 2020, now Pat. No. 11,311,175, which is a continuation of application No. 16/677,410, filed on Nov. 7, 2019, now Pat. No. 10,702,131, which is a
(Continued)

(51) Int. Cl.
A61B 1/00 (2006.01)
A61B 1/04 (2006.01)
A61B 1/227 (2006.01)
A61B 1/233 (2006.01)
A61B 5/00 (2006.01)

(52) U.S. Cl.
CPC ...... *A61B 1/00126* (2013.01); *A61B 1/00009* (2013.01); *A61B 1/0002* (2013.01); *A61B 1/0004* (2022.02); *A61B 1/00042* (2022.02); *A61B 1/00052* (2013.01); *A61B 1/042* (2013.01); *A61B 1/227* (2013.01); *A61B 1/233* (2013.01); *A61B 5/7271* (2013.01); *A61B 5/74* (2013.01); *A61B 5/742* (2013.01); *A61B 5/7425* (2013.01)

(58) Field of Classification Search
CPC ............ A61B 1/00126; A61B 1/00009; A61B 1/0002; A61B 1/0004; A61B 1/00042; A61B 1/00052; A61B 1/042; A61B 1/227; A61B 1/233; A61B 5/7271; A61B 5/74; A61B 5/742; A61B 5/7425
See application file for complete search history.

(56) References Cited

U.S. PATENT DOCUMENTS 9,105,207 B2 8/2015 Leung
9,123,155 B2 9/2015 Cunningham
(Continued)

FOREIGN PATENT DOCUMENTS

CN 105788390 A 7/2016
CN 206431875 U 8/2017
(Continued)

OTHER PUBLICATIONS

US 9,980,782 B1, 05/2018, Gibby (withdrawn)
(Continued)

Primary Examiner — Anne M Hines
Assistant Examiner — Jose M Diaz
(74) Attorney, Agent, or Firm — Miller Johnson

(57) ABSTRACT

An imaging connector includes a proximal side and a distal side. The proximal side includes a light input opening and an image output opening. The distal side includes a light output opening and an image input opening. The imaging connector is operable to (i) transmit light from the light input opening to the light output opening, and (ii) transmit an image from the image input opening to the image output opening.

20 Claims, 7 Drawing Sheets

Related U.S. Application Data continuation of application No. 15/985,040, filed on May 21, 2018, now Pat. No. 10,470,645.

(60) Provisional application No. 62/509,267, filed on May 22, 2017.

(56) References Cited

U.S. PATENT DOCUMENTS

| | | | |
|---|---|---|---|
| 9,547,940 B1 | 1/2017 | Sun | |
| 10,010,379 B1 | 7/2018 | Gibby | |
| 10,154,823 B2 | 12/2018 | Von Berg | |
| 10,194,990 B2 | 2/2019 | Amanatullah | |
| 10,702,131 B2 | 7/2020 | Lo | |
| 11,678,789 B2 * | 6/2023 | Lo | A61B 5/74 362/574 |
| 2011/0313479 A1 | 12/2011 | Rubin | |
| 2013/0038707 A1 | 2/2013 | Cunningham et al. | |
| 2013/0293578 A1 | 11/2013 | Leung | |
| 2016/0135925 A1 | 5/2016 | Mason | |
| 2016/0225192 A1 | 8/2016 | Jones | |
| 2016/0370239 A1 | 12/2016 | Cummings | |
| 2017/0090675 A1 | 3/2017 | Lee | |
| 2017/0252108 A1 | 9/2017 | Rios | |
| 2017/0367771 A1 | 12/2017 | Tako | |
| 2018/0012413 A1 | 1/2018 | Jones | |
| 2018/0012416 A1 | 1/2018 | Jones | |
| 2018/0140362 A1 | 5/2018 | Cali | |
| 2018/0192964 A1 | 7/2018 | Stalder | |
| 2018/0286136 A1 | 10/2018 | Jones | |
| 2019/0080515 A1 | 3/2019 | Geri | |
| 2019/0240508 A1 | 8/2019 | Friman | |
| 2019/0343396 A1 | 11/2019 | Khosravi Simchi et al. | |

FOREIGN PATENT DOCUMENTS

| | | |
|---|---|---|
| CN | 107536643 A | 1/2018 |
| EP | 3423972 A1 | 1/2019 |
| WO | 2002080773 A1 | 10/2002 |
| WO | 2013165408 A1 | 11/2013 |
| WO | 2015145395 A1 | 10/2015 |
| WO | 2016162789 A2 | 10/2016 |
| WO | 2016184704 A1 | 11/2016 |
| WO | 2016140989 A9 | 9/2017 |
| WO | 2017151963 A1 | 9/2017 |
| WO | 2017165301 A1 | 9/2017 |
| WO | 2018162079 A1 | 9/2018 |
| WO | 2018165767 A1 | 9/2018 |
| WO | 2018195529 A1 | 10/2018 |
| WO | 2019053627 A1 | 3/2019 |

OTHER PUBLICATIONS

Non-Final Office Action issued by the U.S. Patent and Trademark Office dated Mar. 26, 2019, relating to U.S. Appl. No. 15/985,040.
USPTO, Final office Action for U.S. Appl. No. 16/514,163, dated Apr. 9, 2020.
USPTO, Non-Final Office Action for U.S. Appl. No. 16/514,163, dated Oct. 16, 2019.
USPTO, Non-Final Office Action for U.S. Appl. No. 16/893,927, dated Aug. 19, 2021.

* cited by examiner

IMAGING SYSTEM AND METHOD

CROSS REFERENCE TO RELATED APPLICATIONS

This U.S. patent application is a continuation of, and claims priority under 35 U.S.C. § 120 from, U.S. patent application Ser. No. 17/704,360, filed Mar. 25, 2022, which is a continuation of, and claims priority under 35 U.S.C. § 120 from, U.S. patent application Ser. No. 16/893,927, filed on Jun. 5, 2020, which is a continuation of, and claims priority under 35 U.S.C. § 120 from, Ser. No. 16/677,410, filed on Nov. 7, 2019, which is a continuation of, and claims priority under 35 U.S.C. § 120 from, U.S. patent application Ser. No. 15/985,040, filed on May 21, 2018, which claims priority under 35 U.S.C. § 119(e) to U.S. Provisional Application 62/509,267, filed on May 22, 2017. The disclosures of these prior applications are considered part of the disclosure of this application and are hereby incorporated by reference in their entireties.

FIELD

The present disclosure relates generally to an imaging system and method, and more particularly to a system and method for capturing and processing images with a personal communication device.

BACKGROUND

This section provides background information related to the present disclosure and is not necessarily prior art.

Medical professionals utilize various types of medical devices, such as scopes, to view, diagnose, and treat medical conditions. For example, an endoscope may be used to examine the interior of a hollow organ or cavity of a patient's body. In particular, a nasopharyngoscope may be used to examine a patient's nasal passages and pharynx. Similarly, an otoscope may be used to examine a patient's ear canal.

Image capturing devices and related systems are, likewise, commonly used in the medical profession to capture images of a patient's body, and, thereafter, diagnose and treat medical conditions. For example, cameras, X-Ray systems, and magnetic resonance imaging systems are used to capture various types of images of a patient's body.

While known medical devices, such as scopes, and known imaging systems have proven acceptable for their intended purposes, a continuous need for improvement in the relevant art remains.

SUMMARY

This section provides a general summary of the disclosure, and is not a comprehensive disclosure of its full scope or all of its features.

One aspect of the disclosure provides an imaging system. The imaging system may include a personal communication device, a scope, and a connector. The personal communication device may include a camera system and a light source. The scope may include an input end, an output end, a light-transmitting portion, and an image-transmitting portion. The light-transmitting portion may be operable to transmit light from the input end to the output end. The image-transmitting portion may be operable to transmit an image from the output end to the input end. The connector may be disposed between the personal communication device and the scope. The connector may include an image transmitter and a light transmitter. The image transmitter may be configured to transmit an image from the scope to the camera system. The light transmitter may be configured to transmit light from the light source to the scope.

Another aspect of the disclosure provides an imaging connector. The imaging connector may include a proximal side and a distal side. The proximal side may include a light input opening and an image output opening. The distal side may include a light output opening and an image input opening. The imaging connector may be operable to transmit light from the light input opening to the light output opening. The imaging connector may be operable to transmit an image from the image input opening to the image output opening.

Implementations of the disclosure may include one or more of the following optional features. In some implementations, the light output opening surrounds the image input opening. The image input opening may be concentrically disposed within the light output opening.

In some implementations, the imaging connector includes a channel and an aperture. The channel may extend from the light input opening to the light output opening. The aperture may extend from the image input opening to the image output opening.

In some implementations, the light input opening is offset from the image output opening by a distance. The distance may be variable.

In some implementations, the imaging connector includes a medial portion and a lateral portion translatably coupled to the medial portion.

Another aspect of the disclosure provides an image-processing system. The image-processing system may include an encryption module, a memory, a processing module, and a comparison module. The encryption module may be operable to encrypt an image. The memory may be operable to store the encrypted image. The processing module may be operable to edit the processed image. The comparison module may be operable to compare the processed image to a pre-selected image.

Yet another aspect of the disclosure provides a method of processing an image. The method may include capturing an image of a first target area. The method may also include encrypting the captured image. The method may further include storing the encrypted image. The method may also include editing the stored image. The method may further include comparing the processed image to a pre-selected image of a second target area.

In some implementations, the first target area is the same as the second target area.

In some implementations, the method includes diagnosing a condition based on a difference between the processed image and the pre-selected image.

Another aspect of the disclosure provides an imaging system comprising a personal communication device, an image-transmitting attachment, and a connector configured to couple the personal communication device to the image-transmitting attachment. The personal communication device may include a smartphone, a tablet computer, or other similar device, having a light source and an image-capturing device (e.g., a camera). The light source may include a circular, single-point light light-emitting diode light source having a first diameter.

The connector may include a channel configured to allow the light source to transmit light. The connector may be configured to transform the circular, single-point light to a circumferential light output having a ring shape. In this regard, the connector may include a light receiver aligned with the light source of the personal communication device. In some implementations, the light receiver defines a circular shape having a second diameter. The second diameter may be equal to the first diameter. In some implementations, the connector may include a plurality of fiber optic strands disposed within the channel and extending from the light receiver to a ring-shaped light output.

The ring-shaped light output may be configured to illuminate a distal end of the image-transmitting attachment. For example, the ring-shaped light output may illuminate a distal end of an otoscope or a distal end of a nasopharyngoscope. The connector may also be configured to align the image-capturing device of the personal communication device with an image transmitting portion of the image-transmitting attachment. For example, the connector may align the image-capturing device with an image-transmitting channel defined by the connector, allowing images from the image-transmitting channel to be captured by the image-capturing device. The light output of the connector may be circumferentially disposed about the image-transmitting channel.

The image-transmitting attachment may include an image guide, a light guide, and a lens. In some implementations, the light guide surrounds the image guide. The light guide may include a light guide surface. In some implementations, the light guide includes an annular channel disposed about the image guide. In some implementations, the light guide may include a plurality of fiber optic strands disposed within the channel. The image guide may include one or more fiber optic strands. For example, the image guide may include a bundle of fiber optic strands about which the light guide is disposed.

The annular channel of the image-transmitting attachment may receive light from the ring-shaped light output end of the connector. In this regard, the connector may be configured to align the ring-shaped light output end with the light guide surface or the annular channel of the image-transmitting attachment, such that the light guide surface receives light from the ring-shaped light output end and transmits the light through the annular channel to the distal end of the image-transmitting attachment to illuminate the target area.

The image guide may include a plurality of fiber optic strands aligned with, coupled to, or disposed within the channel of the connector, such that the image guide is operable to transmit an image from, and of, the target area, through the lens disposed at the distal end of the image-transmitting attachment, back to the channel of the connector and back to the image-capturing device of the personal communication device. In this regard, the channel of the connector may transmit the image to a lens of the image-capturing device.

Yet another aspect of the disclosure provides an image-transmitting attachment, such as a scope (e.g., nasopharyngoscope, otoscope, ophthalmoscope, dermoscope, low-level microscope, etc.), attached to a personal communication device (e.g., a smart phone). Illumination of a target area (e.g., a patient's body) is provided by a light source (e.g., light-emitting diode) of the personal communication device transmitting light via a channel (e.g., a fiber optic light channel) to a distal end of the image-transmitting attachment. An image of the illuminated target area may be carried back through a coherent image-transmitting device (e.g., a fiber optic cable) of the image-transmitting attachment to a lens configured to focus the image for capture by a lens of the personal communication device.

A further aspect of the present disclosure provides an imaging system and method configured to leverage the imaging, storage, processing, and communications capabilities of a personal communication device.

In some implementations, the method may include capturing an image of a target area of a patient. The target area may include a condition.

In some implementations, the method may include storing the captured image in a memory of the personal communication device. For example, the captured image may be encrypted and stored securely in the memory for retrieval using a fingerprint. In some implementations, storage of the captured image may satisfy requirements of the Health Insurance Portability and Accountability Act.

In some implementations, the method may include processing the captured or stored image. For example, the method may include enhancing, marking-up, or "ghosting" the captured or stored image. In particular, the method may include overlaying one of a pre-selected image and the captured or stored image relative to the other of the pre-selected image and the captured or stored image. In some implementations, the pre-selected image may include an image of a target area of a reference or benchmark specimen. The target area of the reference or benchmark specimen may correspond to the target area of the patient. The target area of the reference or benchmark may not include the condition.

In some implementations, the method may include comparing the target area of the patient to the target area of the reference. For example, the method may include determining whether there are any differences between the target area of the patient to the target area of the reference. In particular, the method may include identifying the condition of the target area of the patient relative to the target area of the reference.

In some implementations, the method may include diagnosing the condition. For example, the method may include diagnosing the condition based on the comparison of the target area of the patient to the target area of the reference.

Yet another aspect of the present disclosure provides an imaging system. The imaging system may include a personal communication device and a connector. The personal communication device may include a camera system, a display portion, and a handle portion. The display portion may be configured to display images captured by the camera system. The handle portion may extend from the display portion in a first direction. The connector may extend from the display portion in a second direction transverse to the first direction. The connector may be operable to couple to a scope.

Implementations of this aspect may include one or more of the following features. In some implementations, the display portion defines a circular shape.

In some implementations, the connector includes a lens configured to receive the images.

In some implementations, the connector includes an outer surface extending from a proximal end to a distal end. The proximal end may be supported by the display portion. The distal end may be offset from the proximal end by a distance extending in the second direction. The outer surface may be concave. In some implementations, the outer surface defines a frustoconical shape extending from the proximal end to the distal end. The first direction may be perpendicular to the second direction.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected configurations and not all possible implementations, and are not intended to limit the scope of the present disclosure.

Corresponding reference numerals indicate corresponding parts throughout the drawings.

DETAILED DESCRIPTION

Example configurations will now be described more fully with reference to the accompanying drawings. Example configurations are provided so that this disclosure will be thorough, and will fully convey the scope of the disclosure to those of ordinary skill in the art. Specific details are set forth such as examples of specific components, devices, and methods, to provide a thorough understanding of configurations of the present disclosure. It will be apparent to those of ordinary skill in the art that specific details need not be employed, that example configurations may be embodied in many different forms, and that the specific details and the example configurations should not be construed to limit the scope of the disclosure.

Figure 1:
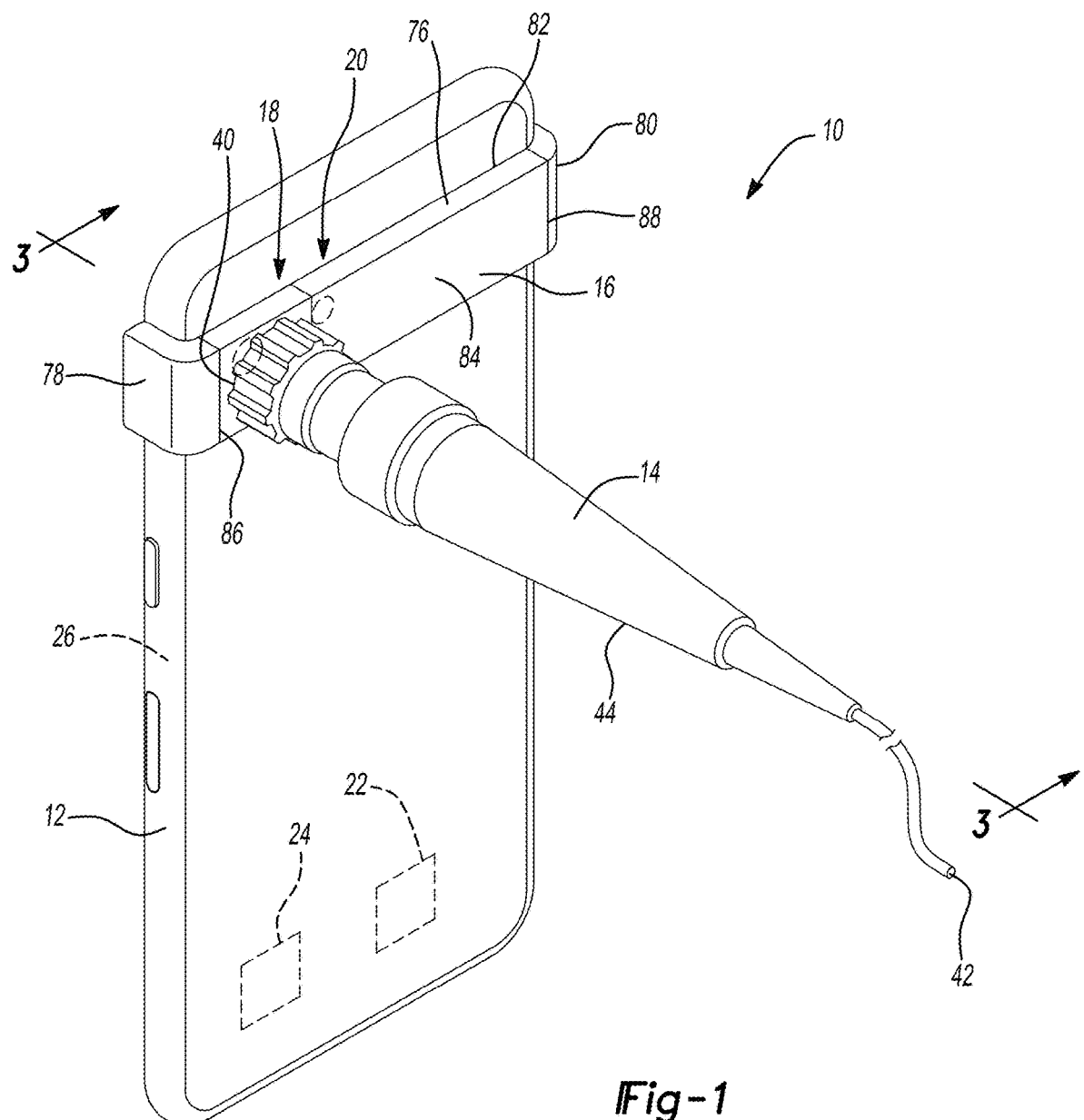
FIG. 1 is a perspective view of an imaging system in accordance with the principles of the present disclosure.
Figure 2:
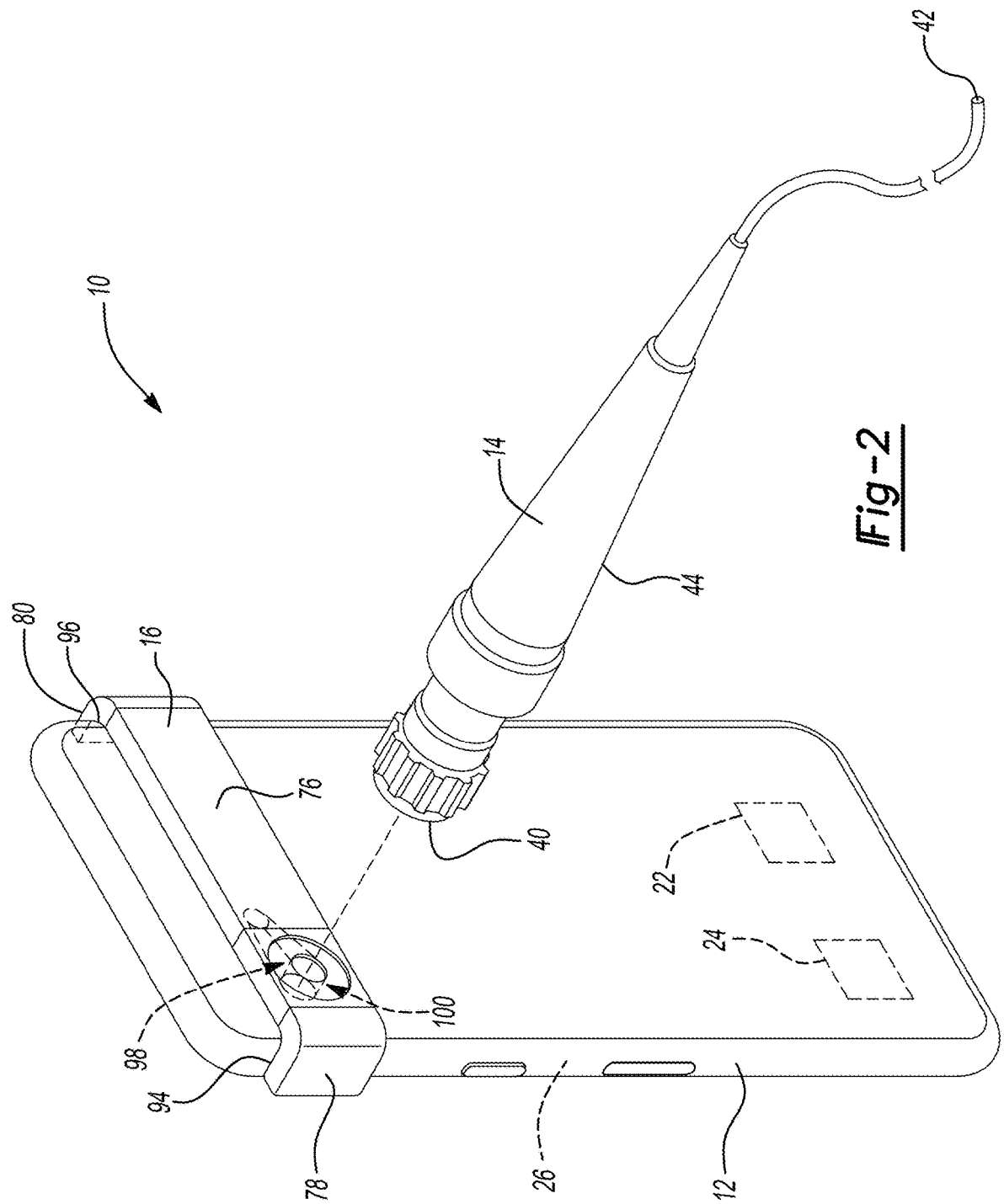
FIG. 2 is a partially exploded view of the imaging system of FIG. 1.
Figure 3:
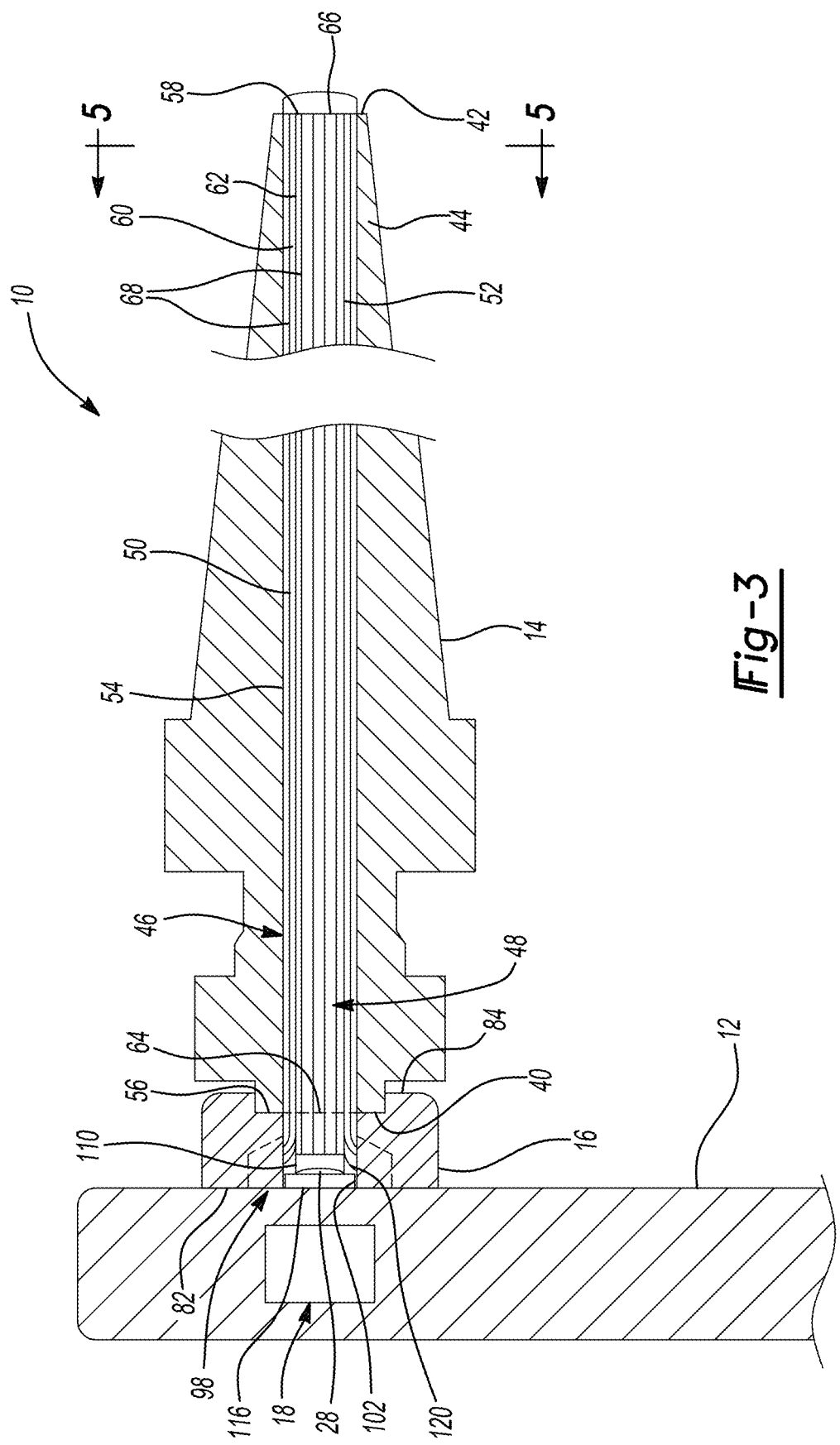
FIG. 3 is a cross-sectional view of the imaging system of FIG. 1 taken through the line 3-3.

With reference to FIGS. 1-3, an imaging system 10 in accordance with the principles of the present disclosure is shown. As will be explained in more detail below, in some implementations, the imaging system 10 may be utilized by a physician or other medical professional in a medical environment in order to capture, store, and process images of a patient. It will be appreciated, however, that the imaging system 10 may be utilized in other environments and by other users within the scope of the present disclosure.

The imaging system 10 may include a personal communication device 12, an image-transmitting device 14, and a connector 16. The personal communication device 12 may be a smartphone, a tablet computer, or other suitable computing device. In this regard, the personal communication device 12 is intended to represent various forms of digital computers, such as smartphones, laptops, desktops, workstations, personal digital assistants, servers, blade servers, mainframes, and other appropriate computers (e.g., personal communication device 12). The components shown here, their connections and relationships, and their functions, are meant to be exemplary only, and are not meant to limit implementations of the inventions described and/or claimed in this document.

Figure 4:
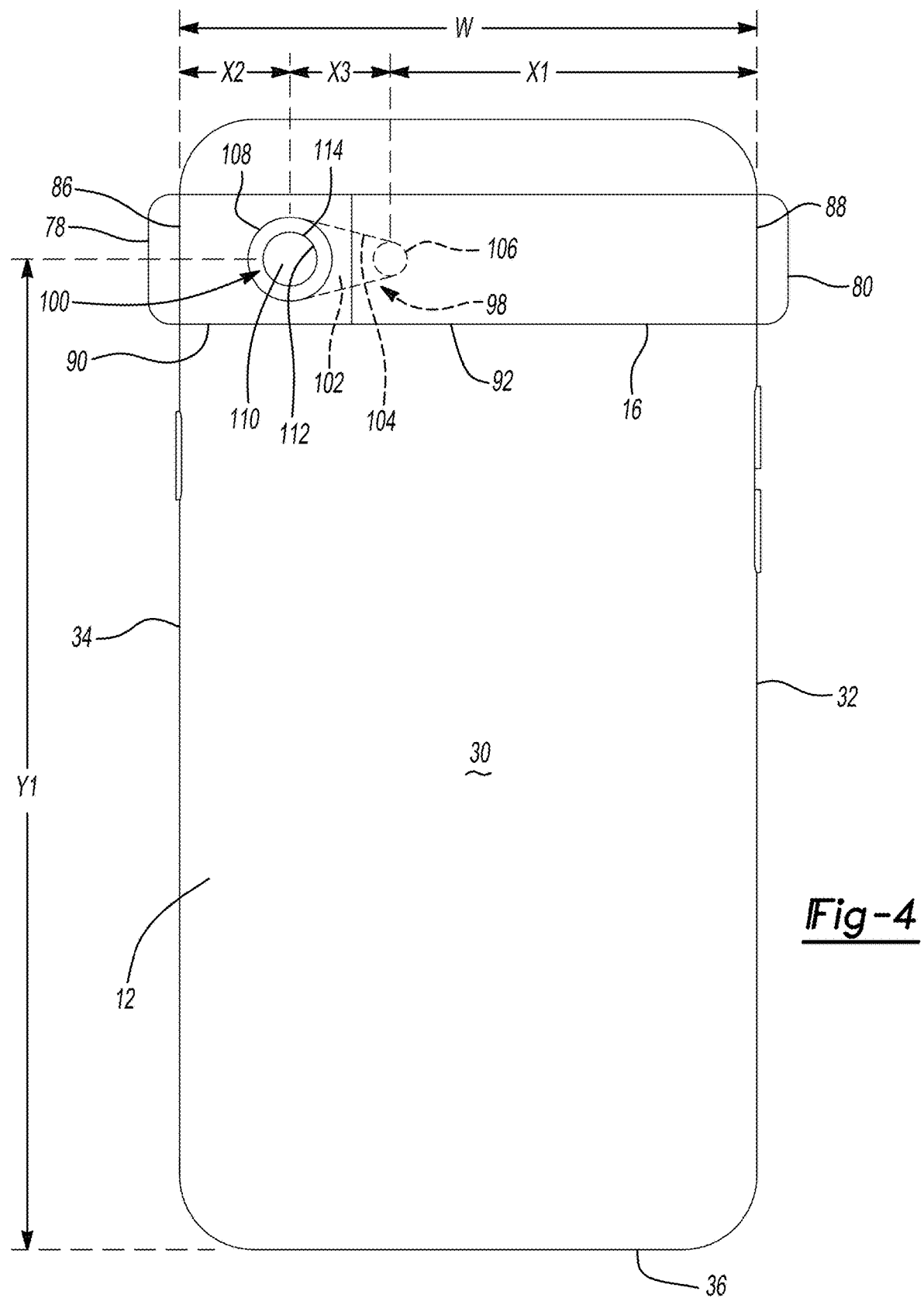
FIG. 4 is a rear view of a personal communication device and a connector of the imaging system of FIG. 1 in accordance with the principles of the present disclosure.

The personal communication device 12 may include a camera system 18, a light source 20, a memory 22, an image-processing system 24, and a display 26. With reference to FIG. 3, the camera system 18 may include a lens 28 through which an image can be transmitted. The light source 20 may include a light-emitting diode (not shown) or other suitable light-producing device. As illustrated in FIG. 4, the light source 20 and the camera system (e.g., the lens 28) may be disposed on a rear surface 30 of the personal communication device 12. In some implementations, the light source 20 is disposed a distance X1 from a medial side 32 of the personal communication device 12, and the lens is disposed a distance X2 from a lateral side 34 of the personal communication device 12. The lateral side 34 may be opposite the medial side 32. The light source 20 and the lens 28 may each be disposed a distance Y1 from an end 36 of the personal communication device 12. The end 36 may extend from and between the lateral and medial sides 32, 34. The light source 20 may be disposed a distance X3 from the lens 28 in a direction transverse (e.g., orthogonal) to the distance Y1. In some implementations, a center of the lens 28 may be collinear with a center of the light source 20 along a line extending perpendicular to the lateral and medial sides 32, 34. It will be appreciated that the distances X1, X2, X3, and Y1 may vary depending on the particular configuration (e.g., size, shape, etc.) of the personal communication device 12 utilized in the imaging system 10.

The image-transmitting device 14 may include a scope, such as a nasopharyngoscope, an otoscope, an ophthalmoscope, a dermoscope, a low-level microscope, or other similar device having an input end 40, an output end 42, and operable to transmit an image from the input end 40 to the output end 42. With particular reference to FIG. 3, the image-transmitting device 14 may include a housing 44 having a light-transmitting portion 46 and an image-transmitting portion 48.

Figure 5:
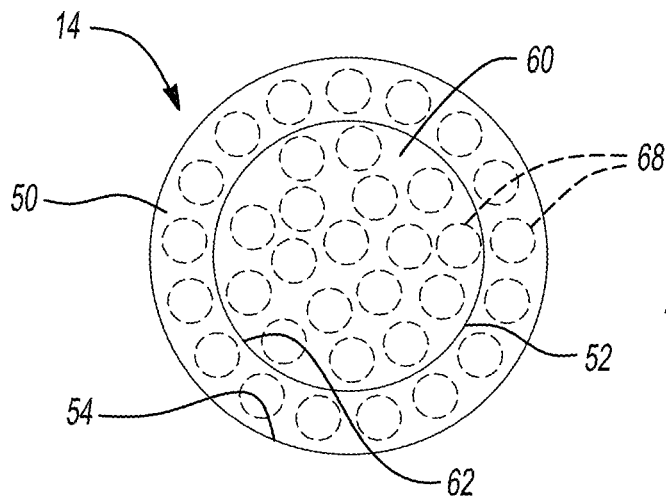
FIG. 5 is a cross-sectional view of an image-transmitting device of the imaging system of FIG. 1 taken through the line 5-5 of FIG. 3.

In some implementations, the light-transmitting portion 46 defines a channel 50 extending from the input end 40 to the output end 42. In this regard, as illustrated in FIG. 5, the channel 50 may be defined by a first inner surface 52 and a second inner surface 54 of the housing 44. In some implementations, the first inner surface 52 defines a cylinder having a first diameter D1, and the second inner surface 54 defines a cylinder having a second diameter D2 that is greater than the first diameter D1, such that the channel 50 defines an annular or hollow cylindrical construct. The first inner surface 52 may be concentrically disposed within the second inner surface 54. The first and second inner surfaces 52, 54 may extend from and between the input and output ends 40, 42 to define light inlet and outlet openings 56, 58, respectively, at the input and output ends 40, 42.

The image-transmitting portion 48 may be concentrically disposed within the light-transmitting portion 46. In this regard, the image-transmitting portion 48 may define an aperture 60 extending from the input end 40 to the output end 42. As illustrated in FIG. 5, the aperture 60 may be defined by a third inner surface 62 of the housing 44. In some implementations, the third inner surface 62 defines a cylinder having a third diameter D3 that is less than the first and second diameters D1, D2 of the light-transmitting portion 46. The third inner surface 62 may extend from and between the input and output ends 40, 42 to define image outlet and inlet openings 64, 66 (FIG. 3), respectively, at the input and output ends 40, 42. The outlet and inlet openings 64, 66 of the image-transmitting portion 48 may be concentrically disposed within the inlet and outlet openings 56, 58 of the light-transmitting portion 46.

The image-transmitting device 14 may also include plurality of elements 68 configured to transmit images or light from the input end 40 to the output end 42, or from the output end 42 to the input end 40, of the image-transmitting device 14. In some implementations, the elements 68 may include fiber optic strands. The elements 68 may include a proximal end disposed proximate the input end 40, and a distal end disposed proximate the output end 42. A first plurality of the elements 68 may be disposed within the light-transmitting portion 46 of the device 14, and a second plurality of the elements 68 may be disposed within the image-transmitting portion 48 of the device 14. In this regard, the first plurality of the elements 68 may be disposed within the channel 50 and the second plurality of the elements may be disposed within the aperture 60, such that the first plurality of the elements 68 surrounds the second plurality of the elements 68.

With reference to FIG. 1, the connector 16 may include a base 76, a lateral arm 78, and a medial arm 80. The base 76 may include a proximal side 82, a distal side 84 opposite the proximal side 82, a lateral end 86, and a medial end 88 opposite the lateral end 86. The lateral and medial ends 86, 88 may extend from and between the proximal and distal sides 82, 84. With reference to FIG. 4, the connector 16 may define a width W extending from the lateral end 86 to the medial end 88. In some implementations, the width W may be adjustable such that a user can vary the width W to equal a width extending from and between the medial and lateral sides 32, 34 of the personal communication device 12. In this regard, the connector 16 may include a lateral portion 90 and a medial portion 92. The lateral portion 90 may be adjustably coupled to the medial portion 92. For example, one of the lateral and medial portions 90, 92 may be supported for translation in a direction substantially parallel to the width W relative to the other of the lateral and medial portions 90, 92, such that the user can vary the width W by translating the lateral portion 90 relative to the medial portion 92. In particular, one of the lateral or medial portions 90, 92 may include male portion and the other of the lateral or medial portions 90, 92 may include female portion that receives the male portion (e.g., a dovetail, tongue in groove, etc.) such that the male portion can slide relative to the female portion.

With reference to FIG. 2, the lateral arm 78 may include a lateral stop surface 94, and the medial arm 80 may include a medial stop surface 96. The lateral arm 78 may be supported by the base 76 proximate to the lateral end 86 and the medial arm 80 may be supported by the base 76 proximate to the medial end 88, such that the width W extends from the lateral stop surface 94 to the medial stop surface 96.

With reference to FIGS. 2-4, the connector 16 may further include a light transmitter 98 and an image transmitter 100. As will be explained in more detail, below, the light transmitter 98 may transmit light from the light source 20 to the light-transmitting portion 46 of the image-transmitting device 14, and the image transmitter 100 may transmit images from the image-transmitting portion 48 of the image-transmitting device 14 to the camera system 18 (e.g., lens 28).

With particular reference to FIG. 3, in some implementations, the light transmitter 98 defines a channel 102 extending from the proximal side 82 to the distal side 84. In this regard, as illustrated in FIG. 4, the channel 102 may be defined by an inner surface 104 of the connector 16. The inner surface 104 may extend from and between the proximal and distal sides 82, 84 to define inlet and outlet openings 106, 108 at the proximal and distal sides 82, 84, respectively. In some implementations, the channel 102 extends through the lateral and medial portions 90, 92 of the connector 16.

With reference to FIG. 3, the image transmitter 100 may define an aperture 110 extending from the proximal side 82 to the distal side 84. As illustrated in FIG. 4, the aperture 110 may be defined by an inner surface 112 of the connector 16. In some implementations, the inner surface 112 defines a cylinder extending from and between the proximal and distal sides 82, 84 to define an inlet opening 114 and an outlet opening 116 at the distal and proximal sides 84, 82, respectively. The inlet opening 114 of the image transmitter 100 may be concentrically disposed within the outlet opening 108 of the light transmitter 98.

As illustrated in FIG. 4, in some implementations, the inlet opening 106 of the light transmitter 98 is disposed on the medial portion 92 of the connector 16 and the outlet opening 116 of the image transmitter 100 is disposed on the lateral portion 92 of the connector 16. Accordingly, a user may adjust the distance between the inlet opening 106 of the light transmitter 98 and the outlet opening 116 of the image transmitter 100 by moving the lateral portion 90 of the connector 16 relative to the medial portion 92 of the connector 16 in the manner previously described.

As illustrated in FIG. 3, the connector 16 may also include plurality of elements 120 configured to transmit images or light from the proximal side 82 to the distal side 84. In some implementations, the elements 120 may be substantially similar to the elements 68, and may include fiber optic strands. A first plurality of the elements 120 may be disposed within the light transmitter 98 of the connector 16, and a second plurality of the elements 120 may be disposed within the image-transmitter 100 of the connector 16. In this regard, the first plurality of the elements 120 may be disposed within the channel 102 and the second plurality of the elements may be disposed within the aperture 110, such that the first plurality of the elements 120 surrounds the second plurality of the elements 120 along at least a portion of the length of the aperture 110.

With reference to FIGS. 2 and 3, in an assembled configuration, the connector 16 may be supported by, or otherwise coupled to, the personal communication device 12, and the image-transmitting device 14 may be supported by, or otherwise coupled to, the connector 16. In particular, the proximal side 82 of the connector 16 may be disposed adjacent the rear surface 30 of the personal communication device 12 such that the inlet opening 106 of the light transmitter 98 is aligned with the light source 20, and the outlet opening 116 of the image transmitter 100 is aligned with the lens 28. Similarly, the input end 40 of the image-transmitting device 14 may be disposed adjacent the distal side 84 of the connector 16 such that the inlet opening 56 of the light-transmitting portion 46 of the image-transmitting device 14 is aligned with the outlet opening 108 of the light transmitter 98 of the connector 16, and the inlet opening 64 of the image-transmitting portion 48 of the image-transmitting device 14 is aligned with the inlet opening 114 of the image transmitter 100 of the connector 16. In this way, the light transmitter 98 of the connector 16 is operable to transmit light to the light-transmitting portion 46 of the device 14, and the image-transmitting portion 48 of the device 14 is operable to transmit images to the image transmitter 100 of the connector 16. Accordingly, the light source 20 can transmit light through the connector 16 and the device 14 to the output end 42 of the device 14, and the camera system 18 (e.g., lens 28) can receive images transmitted from the output end 42 of the device to the proximal side 82 of the connector 16. In particular, the connector 16 transmits (i) light through the elements 120 to the first plurality of elements 68, and (ii) images from the second plurality of elements 68, through the elements 120, to the lens 28.

Figure 6:
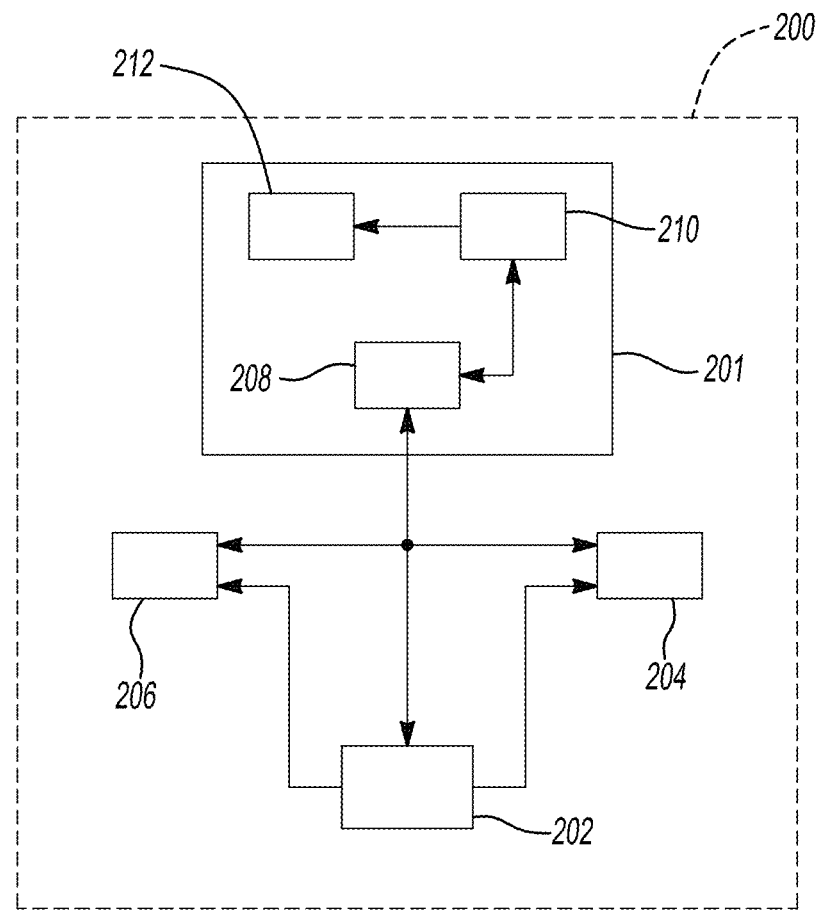
FIG. 6 is a functional block diagram of an example image processing system in accordance with the principles of the present disclosure.

With reference to FIG. 6, an image-processing system 200 is illustrated. The image processing system 200 may include a camera system 201 (e.g., camera system 18), an encryption module 202, a storage device or memory 204, and an image-processing module 206. In some implementations, a computing device, such as the personal communication device 12, or other suitable computer, may implement, or otherwise include, the image-processing system 200. In this regard, the memory 204 may correspond to the memory 22, and the image-processing system 200 may correspond to the image-processing system 24. Each of the components 201, 202, 204, and 206, may be interconnected using various busses, and may be mounted on a common motherboard or in other manners as appropriate. In this regard, the image-processing system 200 and the components thereof may be implemented in a processor that can process instructions for execution within the personal communication device 12, including instructions stored in the memory 204 to display graphical information for a graphical user interface (GUI) on an external input/output device, such as the display 26. In other implementations, multiple processors and/or multiple buses may be used, as appropriate, along with multiple memories and types of memory.

The memory 204 may store information non-transitorily within the image-processing system 200 (e.g., personal communication device 12). In this regard, the memory 204 may communication with the camera system 201, the encryption module 202, and the image-processing module 206. The memory 204 may be a computer-readable medium, a volatile memory unit(s), or non-volatile memory unit(s). The non-transitory memory 204 may be physical devices used to store programs (e.g., sequences of instructions) or data (e.g., program state information) on a temporary or permanent basis for use by the image-processing system 200. Examples of non-volatile memory include, but are not limited to, flash memory and read-only memory (ROM)/ programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The memory 204 may be capable of providing mass storage for the image-processing system 200. In some implementations, the memory 204 is a computer-readable medium. In various different implementations, the memory 204 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described below. The information carrier is a computer- or machine-readable medium, such as the memory 204 or memory on image-processing module 206.

The encryption module 202 may communicate with the camera system 201, the memory 204, and the image-processing module 206. In some implementations, the encryption module 202 receives and encrypts a captured image from the camera system 201 prior to transmitting the encrypted image to the memory 204 for storage. For example, the captured image may be encrypted and stored securely in the memory 204 for retrieval using a fingerprint. In some implementations, storage of the captured image in the memory 204 may satisfy requirements of the Health Insurance Portability and Accountability Act.

The image-processing module 206 may communicate with the camera system 201, the encryption module 202, and the memory 204. In some implementations, the image-processing module 206 receives an image from the camera system 201, or an encrypted image from the encryption module 202, prior to processing the image. The image-processing module 206 may include an editing module 208, a comparison module 210, and a diagnostic module 212. The editing module 208 may edit an image (e.g., an image of a target area of a patient) received from the camera system 201 and/or the memory 204 to produce an edited image. For example, the editing module 208 may receive an image of a target area (e.g., an internal organ) of a patient captured by the camera system 201, and thereafter enhance, mark-up, or ghost the captured image. In some implementations, the editing module 208 may overlay one of a pre-selected image and the captured image relative to the other of the pre-selected image and the captured image.

The comparison module 210 may communicate with the editing module 208. For example, the comparison module 210 may receive the captured image (e.g., the edited image) from the editing module 208. The comparison module 210 may compare the captured image to a pre-selected image. In particular, the comparison module 210 may determine whether the captured image matches or appears similar (e.g., identical) to the pre-selected image. The pre-selected image may include a reference or benchmark image of a target area (e.g., an internal organ). In this regard, the pre-selected image may correspond to a normal or ideal image of the target area. In some implementations, the comparison module 210 may output the differences between the captured image and the pre-selected image.

The diagnostic module 212 may communicate with the comparison module 210. For example, the diagnostic module 212 may receive the differences between the captured image and the pre-selected image from the comparison module. The diagnostic module 212 may diagnose a condition corresponding to the captured image. For example, the diagnostic module 212 may determine a disease or other abnormality of the target area based on the differences between the captured image and the pre-selected image.

Figure 7:
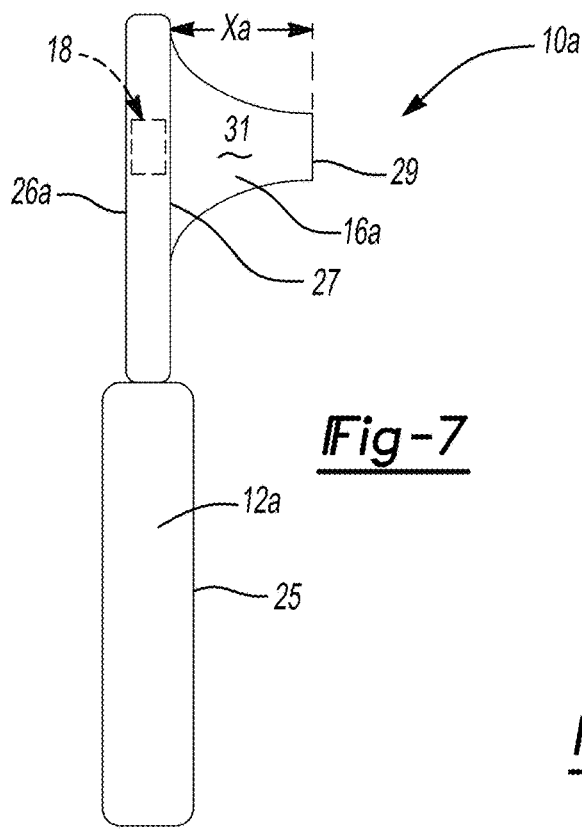
FIG. 7 is a side view of another imaging system in accordance with the principles of the present disclosure.
Figure 8:
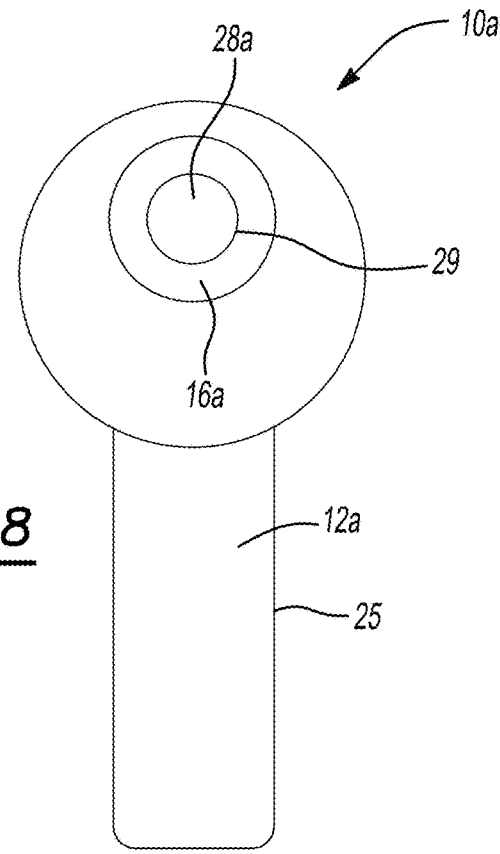
FIG. 8 is a front view of the imaging system of FIG. 7.
Figure 9:
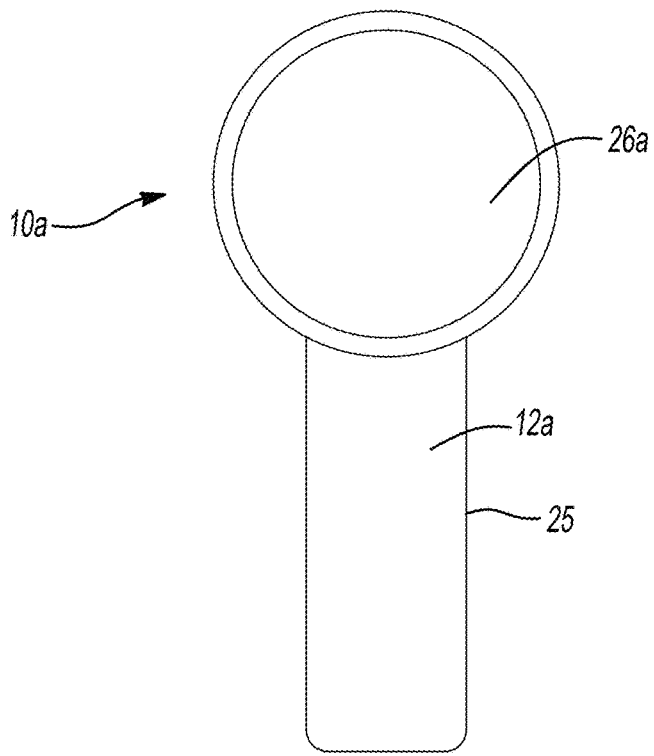
FIG. 9 is a rear view of the imaging system of FIG. 7.

With reference to FIGS. 7-9, another imaging system 10*a* for use with the image-transmitting device 14 is shown. The structure and function of the imaging system 10*a* may be substantially similar to that of the imaging system 10, apart from any exceptions described below and/or shown in the Figures. Accordingly, the structure and/or function of similar features will not be described again in detail. In addition, like reference numerals are used hereinafter and in the drawings to identify like features, while like reference numerals containing letter extensions (i.e., "a") are used to identify those features that have been modified.

The imaging system 10*a* may include a personal communication device 12*a* and a connector 16*a*. As previously described relative to the imaging system 10, in an assembled configuration, the connector 16*a* may be supported by, or otherwise coupled to, the personal communication device 12*a*, and the image-transmitting device 14 may be supported by, or otherwise coupled to, the connector 16*a*.

The personal communication device 12*a* may be a smartphone, a tablet computer, or other suitable computing device. In this regard, the personal communication device 12*a* may be substantially similar to the personal communication device 12 and is intended to represent various forms of digital computers, such as smartphones, laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The personal communication device 12*a* may further include a handle portion 25 and a display portion 26*a*. The handle portion 25 may extend from the display portion 26*a* in a first direction and may be sized and shaped to allow a user to comfortably grip the handle portion 25 in the user's hand.

The display portion 26*a* may be coupled to the handle portion 25 and may include a graphical user interface (GUI) for displaying graphical information (e.g., images) on an external input/output device. For example, as previously described relative to the imaging system 10, the display portion 26*a* may display images captured by a camera system (e.g., camera system 18). As illustrated in FIGS. 8 and 9, in some implementations, the display portion 26*a* defines a circular shape or construct having a diameter between two inches and three inches. For example, the diameter of the display portion 26*a* may be substantially equal to two and one-half inches. It will be appreciated, however, that the display portion 26*a* may define other shapes (e.g., an oval, a rectangle, or other polygon) within the scope of the present disclosure.

The connector 16*a* may be supported by the display portion 26*a* and may include a lens 28*a* through which an image can be transmitted to the camera system 18. In some implementations, a proximal end 27 of the connector 16*a* is coupled to the display portion 26*a*, and a distal end 29 of the connector 16*a* is offset from the display portion by a distance Xa. In this regard, the connector 16*a* may protrude outwardly from the display portion 26*a* by the distance Xa in a second direction that is transverse (e.g., perpendicular) to the first direction. The distance Xa may be between ten millimeters and fifty millimeters. In some implementations the distance is substantially equal to thirty millimeters.

The connector 16*a* may include an outer surface 31. In some implementations, the outer surface 31 is concave. For example, the outer surface 31 may define a frustoconical shape extending from the proximal end 27 to the distal end 29.

Figure 10:
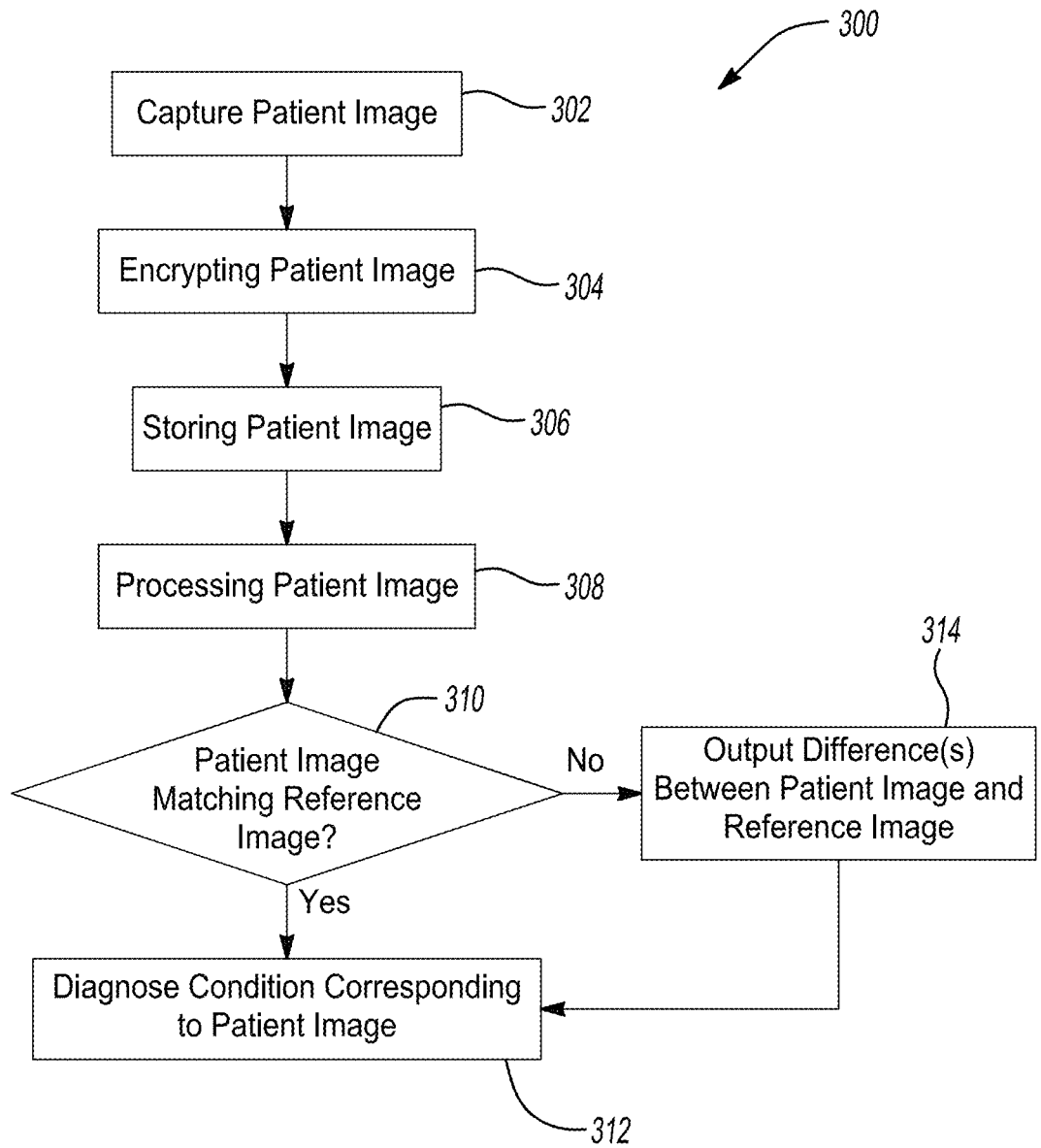
FIG. 10 is a flowchart illustrated an example image processing method in accordance with the principles of the present disclosure.

With reference to FIG. 10, an image-processing method 300 in accordance with the principles of the present disclosure is illustrated. The method 300 may be implemented by the system 200. In this regard, in some implementations, the method 300 is implemented by the imaging system 10, 10*a* (e.g., the personal communication device 12, 12*a*).

At step 302, the method 300 may include capturing an image. For example, the method may include capturing an image of a patient. In particular, at step 302, the method may include capturing an image of a target area (e.g., an organ or portion thereof) of a patient utilizing the camera system 18, 201.

At step 304, the method 300 may include encrypting an image. For example, the method may include encrypting an image of a target area of a patient. In some implementations, at step 304, the method includes encrypting the image of the target area captured at step 302. In particular, step 304 may include encrypting the image of the target area utilizing the encryption module 202.

At step 306, the method 300 may include storing an image. For example, the method may include storing an image of a target area of a patient. In some implementations, at step 306, the method includes storing the encrypted image of the target area encrypted at step 304. In particular, step 306 may include securely storing the encrypted image in the memory 204 for retrieval using a fingerprint or other access credentials (e.g., password).

At step 308, the method 300 may include processing an image. For example, the method may include processing an image of a target area of a patient. In some implementations, at step 308, the method includes editing the image stored at step 306 to produce an edited image. In particular, step 308 may include enhancing, marking-up, or ghosting the stored image with the image-processing module 206. For example, at step 308, the editing module 208 may overlay one of a pre-selected image and the captured image relative to the other of the pre-selected image and the captured image. The pre-selected image may include a benchmark or reference image of the target area. In some implementations, the pre-selected image may include a previously-captured image of the target area of the patient.

At step 310, the method 300 may include comparing an image to a pre-selected image. For example, the method may include comparing a captured image of a target area of a patient to a pre-selected image of the target area. In particular, step 310 may include determining whether the image processed at step 308 matches (e.g., appears similar or identical to) the pre-selected image of the target area. If step 310 is true, the method may proceed to step 312. If step 310 is false, the method may proceed to step 314.

At step 314, the method may include outputting differences between an image and a pre-selected image. For example, the method may include outputting differences between an image of a target area of a patient and a pre-selected image of a target area. In some implementations, at step 314, the method may include identifying and/or outputting differences between the image processed at step 308 and the pre-selected image of the target area.

At step 316, the method may include diagnosing a condition of the target area of the patient. For example, the method may include diagnosing a disease or other abnormality of the target area of the patient. In some implementations, at step 316, the method may include diagnosing the condition based on the differences identified at step 314.

The imaging system 10, including the image-processing system 200, and the image-processing method 300 may allow a user (e.g., a medical professional) to efficiently and accurately capture images (e.g., images of a patient), process the images, and diagnose conditions based on the images.

The foregoing description has been provided for purposes of illustration and description. It is not intended to be exhaustive or to limit the disclosure. Individual elements or features of a particular configuration are generally not limited to that particular configuration, but, where applicable, are interchangeable and can be used in a selected configuration, even if not specifically shown or described.

The same may also be varied in many ways. Such variations are not to be regarded as a departure from the disclosure, and all such modifications are intended to be included within the scope of the disclosure.

A software application (i.e., a software resource) may refer to computer software that causes a computing device to perform a task. In some examples, a software application may be referred to as an "application," an "app," or a "program." Example applications include, but are not limited to, system diagnostic applications, system management applications, system maintenance applications, word processing applications, spreadsheet applications, messaging applications, media streaming applications, social networking applications, and gaming applications.

The non-transitory memory may be physical devices used to store programs (e.g., sequences of instructions) or data (e.g., program state information) on a temporary or permanent basis for use by a computing device. The non-transitory memory may be volatile and/or non-volatile addressable semiconductor memory. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The terminology used herein is for the purpose of describing particular exemplary configurations only and is not intended to be limiting. As used herein, the singular articles "a," "an," and "the" may be intended to include the plural forms as well, unless the context clearly indicates otherwise. The terms "comprises," "comprising," "including," and "having," are inclusive and therefore specify the presence of features, steps, operations, elements, and/or components, but do not preclude the presence or addition of one or more other features, steps, operations, elements, components, and/or groups thereof. The method steps, processes, and operations described herein are not to be construed as necessarily requiring their performance in the particular order discussed or illustrated, unless specifically identified as an order of performance. Additional or alternative steps may be employed.

When an element or layer is referred to as being "on," "engaged to," "connected to," "attached to," or "coupled to" another element or layer, it may be directly on, engaged, connected, attached, or coupled to the other element or layer, or intervening elements or layers may be present. In contrast, when an element is referred to as being "directly on," "directly engaged to," "directly connected to," "directly attached to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The terms first, second, third, etc. may be used herein to describe various elements, components, regions, layers and/or sections. These elements, components, regions, layers and/or sections should not be limited by these terms. These terms may be only used to distinguish one element, component, region, layer or section from another region, layer or section. Terms such as "first," "second," and other numerical terms do not imply a sequence or order unless clearly indicated by the context. Thus, a first element, component, region, layer or section discussed below could be termed a second element, component, region, layer or section without departing from the teachings of the example configurations.

What is claimed is:

1. A system comprising:
   at least one processor; and
   memory in communication with the at least one processor, the memory storing instructions that when executed on the at least one processor cause the at least one processor to perform operations comprising:
   receiving an image from an image capturing device, the image corresponding to a target area of a patient;
   comparing the received image to a reference image, the reference image corresponding to a normality of the target area;
   determining a difference between the received image and the reference image; and
   identifying a disease or other abnormality based on the difference between the received image and the reference image.

2. The system of claim 1, wherein the operations further comprise encrypting the received image of the target area of the patient.

3. The system of claim 1, wherein the operations further comprise editing the received image of the target area of the patient.

4. The system of claim 3, wherein editing the received image includes at least one of enhancing or marking-up the received image.

5. The system of claim 3, wherein editing the received image includes editing only a portion of the received image.

6. The system of claim 1, further comprising overlaying one of the received image or the reference image relative to the other of the received image or the reference image.

7. The system of claim 1, further comprising a personal communication device comprising the at least one processor and the memory.

8. The system of claim 1, wherein the operations further comprise storing the received image in the memory.

9. The system of claim 8, wherein the operations further comprise retrieving the received image from the memory based on a fingerprint.

10. The system of claim 1, wherein the reference image is a previously-captured image of the target area of the patient.

11. A method comprising:
    receiving, at at least one processor, an image from an image capturing device, the image corresponding to a target area of a patient;
    comparing, at the at least one processor, the received image to a reference image, the reference image corresponding to a normality of the target area;
    determining, by the at least one processor, a difference between the received image and the reference image; and
    identifying a disease or other abnormality based on the difference between the received image and the reference image.

12. The method of claim 11, further comprising encrypting, by the at least one processor, the received image of the target area of the patient.

13. The method of claim 11, further comprising editing, by the at least one processor, the received image of the target area of the patient.

14. The method of claim 13, wherein editing the received image includes at least one of enhancing or marking-up the received image.

15. The method of claim 13, wherein editing the received image includes modifying only a portion of the received image.

16. The method of claim 11, further comprising overlaying one of the received image or the reference image relative to the other of the received image or the reference image.

17. The method of claim 11, wherein a personal communication device comprises the at least one processor and memory in communication with the at least one processor, the memory storing instructions configured to be executed by the at least one processor.

18. The method of claim 11, further comprising storing, by the at least one processor, the received image in memory in communication with the at least one processor.

19. The method of claim 18, further comprising retrieving, by the at least one processor, the received image from the memory based on a fingerprint.

20. The method of claim 11, wherein the reference image is a previously-captured image of the target area of the patient.

* * * * *